United States Patent
Gelfand et al.

(10) Patent No.: US 7,758,563 B2
(45) Date of Patent: *Jul. 20, 2010

(54) PATIENT HYDRATION MONITORING AND MAINTENANCE SYSTEM AND METHOD FOR USE WITH ADMINISTRATION OF A DIURETIC

(75) Inventors: Mark Gelfand, New York, NY (US);
Robert I. Rudko, Holliston, MA (US);
Mark R. Tauscher, Medfield, MA (US);
Howard R. Levin, Teaneck, NJ (US);
Andy Halpert, Brookline, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 11/823,596

(22) Filed: Jun. 28, 2007

(65) Prior Publication Data

US 2008/0033394 A1    Feb. 7, 2008

Related U.S. Application Data

(63) Continuation-in-part of application No. 10/936,945, filed on Sep. 9, 2004.

(51) Int. Cl.
*A61M 31/00* (2006.01)
*A61M 1/00* (2006.01)

(52) U.S. Cl. .................. 604/503; 604/67; 604/31

(58) Field of Classification Search ............ 604/65–67, 604/30, 31, 503, 506, 508, 517, 245
See application file for complete search history.

(56) References Cited

U.S. PATENT DOCUMENTS

| | | | |
|---|---|---|---|
| 3,954,010 | A | 5/1976 | Hilblom |
| 4,132,644 | A | 1/1979 | Kolberg |
| 4,146,029 | A | 3/1979 | Elinwood, Jr. |
| 4,204,957 | A | 5/1980 | Weickhardt |
| 4,216,462 | A | 8/1980 | McGrath et al. |
| 4,229,299 | A | 10/1980 | Savitz et al. |

(Continued)

FOREIGN PATENT DOCUMENTS

EP     0258690     3/1988
WO   WO 2006/041496 A1   4/2006

OTHER PUBLICATIONS

"Effects of saline, mannitol, and furosemide to prevent acute decreases in renal function induced by radiocontrast agents", Solomon et al., N Engl J Med, 1994; 331:1416-1420.

(Continued)

*Primary Examiner*—Kevin C Sirmons
*Assistant Examiner*—Catherine N Witczak
(74) *Attorney, Agent, or Firm*—Iandiorio & Teska & Coleman

(57) ABSTRACT

A patient hydration system with an infusion subsystem responsive to a source of hydration fluid for infusing the patient with hydration fluid. A urine output measurement subsystem determines the amount of urine output by the patient. A setting is received corresponding to an amount of urine to be output by the patient. When or after the urine output measurement subsystem indicates the set amount of urine has been output by the patient, the infusion subsystem is controlled to administer hydration fluid to the patient based on the patient's further urine output.

1 Claim, 4 Drawing Sheets

U.S. PATENT DOCUMENTS

| | | | |
|---|---|---|---|
| 4,261,360 A | | 4/1981 | Perez |
| 4,275,726 A | | 6/1981 | Schael |
| 4,291,692 A | * | 9/1981 | Bowman et al. ............. 604/31 |
| 4,343,316 A | | 8/1982 | Jespersen |
| 4,448,207 A | | 5/1984 | Parrish |
| 4,449,538 A | | 5/1984 | Corbitt et al. |
| 4,504,263 A | | 3/1985 | Steuer et al. |
| 4,658,834 A | | 4/1987 | Blankenship et al. |
| 4,712,567 A | | 12/1987 | Gille et al. |
| 4,728,433 A | | 3/1988 | Buck et al. |
| 4,813,925 A | | 3/1989 | Anderson, Jr. et al. |
| 4,923,598 A | | 5/1990 | Schal |
| 4,994,026 A | * | 2/1991 | Fecondini ................ 604/29 |
| 5,098,379 A | | 3/1992 | Conway et al. |
| 5,176,148 A | | 1/1993 | Wiest et al. |
| 5,207,642 A | | 5/1993 | Orkin et al. |
| 5,722,947 A | | 3/1998 | Jeppsson et al. |
| 5,769,087 A | | 6/1998 | Westphal et al. |
| 5,814,009 A | | 9/1998 | Wheatman |
| 5,891,051 A | | 4/1999 | Han et al. |
| 5,910,252 A | | 6/1999 | Truitt et al. |
| 5,916,153 A | | 6/1999 | Rhea, Jr. |
| 5,916,195 A | | 6/1999 | Eshel et al. |
| 5,981,051 A | | 11/1999 | Motegi et al. |
| 6,010,454 A | | 1/2000 | Arieff et al. |
| 6,171,253 B1 | | 1/2001 | Bullister et al. |
| 6,231,551 B1 | | 5/2001 | Barbut |
| 6,272,930 B1 | | 8/2001 | Crozafon |
| 6,514,226 B1 | | 2/2003 | Levin et al. |
| 6,537,244 B2 | | 3/2003 | Paukovits et al. |
| 6,551,313 B1 | | 4/2003 | Levin |
| 6,554,791 B1 | | 4/2003 | Cartledge et al. |
| 6,640,649 B1 | | 11/2003 | Paz |
| 6,740,072 B2 | | 5/2004 | Starkweather et al. |
| 6,752,779 B2 | | 6/2004 | Paukovits et al. |
| 6,796,960 B2 | | 9/2004 | Cioanta |
| 6,827,702 B2 | | 12/2004 | Lebel |
| 6,942,637 B2 | | 9/2005 | Cartledge et al. |
| 7,029,456 B2 | | 4/2006 | Ware et al. |
| 7,044,002 B2 | | 5/2006 | Ericson |
| 7,137,964 B2 | | 11/2006 | Flaherty |
| 7,278,983 B2 | | 10/2007 | Ireland et al. |
| 2002/0025597 A1 | | 2/2002 | Matsuda |
| 2002/0072647 A1 | | 6/2002 | Schock et al. |
| 2002/0107536 A1 | | 8/2002 | Hussein |
| 2002/0151834 A1 | | 10/2002 | Utterberg |
| 2002/0161314 A1 | | 10/2002 | Sarajarvi |
| 2003/0048185 A1 | | 3/2003 | Citrenbaum et al. |
| 2003/0048432 A1 | | 3/2003 | Jeng et al. |
| 2003/0114786 A1 | | 6/2003 | Hiller et al. |
| 2004/0025597 A1 | | 2/2004 | Ericson et al. |
| 2004/0059295 A1 | | 3/2004 | Cartledge et al. |
| 2004/0081585 A1 | | 4/2004 | Reid |
| 2004/0087894 A1 | | 5/2004 | Flaherty |
| 2004/0122353 A1 | | 6/2004 | Shahirian et al. |
| 2004/0163655 A1 | | 8/2004 | Gelfand et al. |
| 2004/0167415 A1 | | 8/2004 | Gelfand et al. |
| 2004/0167464 A1 | | 8/2004 | Ireland et al. |
| 2004/0176703 A1 | | 9/2004 | Christensen et al. |
| 2004/0193328 A1 | | 9/2004 | Zaitsu et al. |
| 2004/0243075 A1 | | 12/2004 | Harvie |
| 2005/0027254 A1 | | 2/2005 | Vasko |
| 2005/0065464 A1 | | 3/2005 | Talbot et al. |
| 2006/0052764 A1 | | 3/2006 | Gelfand et al. |
| 2006/0064053 A1 | | 3/2006 | Bollish et al. |
| 2006/0184084 A1 | | 8/2006 | Ware et al. |
| 2006/0235353 A1 | | 10/2006 | Gelfand et al. |
| 2006/0253064 A1 | | 11/2006 | Gelfand et al. |
| 2006/0270971 A1 | | 11/2006 | Gelfand et al. |
| 2007/0088333 A1 | | 4/2007 | Levin et al. |
| 2008/0027409 A1 | | 1/2008 | Rudko et al. |
| 2008/0033394 A1 | | 2/2008 | Gelfand et al. |
| 2008/0221512 A1 | | 9/2008 | Da Silva et al. |

OTHER PUBLICATIONS

"Potential deleterious effect of furosemide in radiocontrast nephropathy", Weinstein et al., Nephron 1992; 62:413-415.

"The Influence of Drug Input Rate on the Development of Tolerance to Furosemide", Wakelkamp et. al., Br J Clin. Pharmacol. 1998; 46: 479-487.

"A Prospective Randomized Trial of Prevention Measures in Patients at High Risk for Contrast Nephropathy, Results of the PRINCE. Study", Stevens et al., JACC vol. 33, No. 2, Feb. 1999:403-11.

Office Action of the Canadian Intellectual Property Office for Canadian Patent Application No. 2,579,829 mailed Jun. 13, 2008 (two (2) pages).

Written Opinion of the International Searching Authority for PCT Application No. PCT/US05/08948 mailed Oct. 3, 2006 (five (5) pages).

Written Opinion of the International Searching Authority for PCT Application No. PCT/US2007/009683 mailed Nov. 24, 2008 (eight (8) pages).

Written Opinion of the International Searching Authority for PCT Application No. PCT/US07/09685 mailed Jul. 18, 2008 (twelve (12) pages).

Written Opinion of the International Searching Authority for PCT Application No. PCT/US07/09684 mailed Jul. 21, 2008 (nine (9) pages).

Written Opinion of the International Searching Authority for PCT Application No. PCT/US08/07845 mailed Sep. 17, 2008 (seven (7) pages).

Written Opinion of the International Searching Authority for PCT Application No. PCT/US08/07841 mailed Sep. 18, 2008 (six (6) pages).

Written Opinion of the International Searching Authority for PCT Application No. PCT/US09/02739 mailed Jun. 19, 2009 (six (6) pages).

Written Opinion of the International Searching Authority for PCT Application No. PCT/US2007/021791 mailed May 8, 2008 (nine (9) pages).

Merit Medical Systems, Inc. 2003 Annual Report: Balloon Inflation Devices & Pressure Monitoring Syringes; Transducers and Accessories, http://www.corporatewindow.com/annuals/mmsi03/10kpage5.html (3 pages).

Rihal et al., "Incidence and Prognostic Importance of Acute Renal Failure After Percutaneous Coronary Intervention", Circulation, May 14, 2002, pp. 2259-2264.

Rosamilia et al., "Electromotive Drug Administration of Lidocaine and Dexamethasone Followed by Cystodistension in Women With Interstitial Cystitis", International Urogynecological Journal Pelvic Floor Dysfunction 1997; 8(3): Abstract of pp. 142-145.

Lelarge et al., "Acute Unilateral Renal Failure and Contralateral Ureteral Obstruction", American Journal of Kidney Diseases, vol. XX, No. 3, Sep. 1992, pp. 286-288.

Doty et al., "Effect of Increased Real Venous Pressure on Renal Function", Journal of Trauma: Injury, Infection and Critical Care, vol. 47, No. 6, Dec. 1999, pp. 1000-1003.

Edelson et al., "Pharmacokinetics of Iohexol, a New Nonionic Radiocontrast Agent, in Humans", Journal of Pharmaceutical Sciences, vol. 73, No. 7, Jul. 1984, pp. 993-995.

Hvistendahl et al., "Renal Hemodynamic Response to Gradated Ureter Obstruction in the Pig", Nephron 1996; 74, pp. 168-174.

Pedersen et al., "Renal Water and Sodium Handling During Gradated Unilateral Ureter Obstruction", Scand J Urol Nephrol 2002; 36, pp. 163-172.

Brezis et al., "Hypoxia of the Renal Medulla—its Implications for Disease", New Enlgand Journal of Medicine, vol. 322, No. 10, Mar. 9, 1995, pp. 647-655.

Heyman et al., "Pathophysiology Of Radiocontrast Nephropathy: A Role For Medullary Hypoxia", Investigative Radiology, vol. 34, No. 11, Nov. 1999, pp. 685-691.

James M. Gloor and Vincente E. Torres, "Reflux and Obstructive Nephropathy, Atlas of Diseases of the Kidney", on-line edition, vol. Two, Section I, Ch. 8, pp. 8.1-8.25 (date unknown).

* cited by examiner

PATIENT HYDRATION MONITORING AND MAINTENANCE SYSTEM AND METHOD FOR USE WITH ADMINISTRATION OF A DIURETIC

RELATED APPLICATIONS

This application is a continuation-in-part application of U.S. patent application Ser. No. 10/936,945, filed Sep. 9, 2004, entitled "Patient Hydration System and Method". This application is also related to co-pending application Ser. Nos. 11/408,851; 11/408,391; 11/409,171; and 11/580,354 all of which are incorporated herein by this reference.

FIELD OF THE INVENTION

This invention relates to a patient hydration system and method.

BACKGROUND OF THE INVENTION

The "cath lab" in a hospital is where a patient is injected with a radiocontrast media, imaged, diagnosed, and often operated on. Typically, a cardiologist refers the patient to the cath lab and the patient is instructed not to eat or drink the night before. In the case of a patient suffering a heart attack, the patient may be transferred directly to the cath lab.

Often, the patient is dehydrated when the patient arrives at the cath lab. The patient is prepped and the radiocontrast media injected. If, after diagnostic imaging, a possible problem is detected, intervention occurs in the form of angioplasty or the placement of a stent. During these procedures, additional radiocontrast media may be injected into the patient and the patient imaged so the interventional cardiologist or radiologist can view the progress of the operation.

Unfortunately, the radiocontrast media can be toxic to the patient especially a patient who is dehydrated at the time the radiocontrast media is injected. A patient who already suffers from various medical problems such as diabetes or kidney problems is even more prone to medical problems due to the injection of the radiocontrast media.

It has been observed that dehydration increases the risk of radiocontrast nephropathy (RCN) when radiocontrast agents are injected into a patient during coronary and peripheral vascular catheterization procedures. RCN is the third most common cause of hospital-acquired renal failure. It occurs in over 5% of patients with any baseline renal insufficiency and can occur in 50% of patients with preexisting chronic renal insufficiency and diabetes. Radiocontrast media has a variety of physiologic effects believed to contribute to the development of RCN. One of the main contributors is renal medullary ischemia, which results from a severe, radiocontrast-induced reduction in renal/intrarenal blood flow and oxygen delivery. The medullary ischemia induces ischemia and/or death of the metabolically active areas of the medulla responsible for urine formation, called the renal tubules. Medullary ischemia is attributed to the increase of oxygen demand by the kidney struggling to remove the radiocontrast media from blood plasma and excrete it from the body at the same time as the normal process of controlling the concentration of urine. Oxygen consumption in the medulla of the kidney is directly related to the work of concentrating urine. Since the presence of radiocontrast media in the urine makes it much more difficult for the kidney to concentrate urine, the work of the medulla outstrips the available oxygen supply and leads to medullary ischemia.

Although the exact mechanisms of RCN remain unknown, it has been consistently observed that patients with high urine output are less vulnerable to contrast injury. It is also clear that dehydration increases the risk of RCN, likely because urine (and contrast media inside the kidney) is excessively concentrated. As a result, patients predisposed to RCN are hydrated via intravenous infusion of normal saline before, during and after the angiographic procedure. Hydration is commonly performed at a conservative rate, especially in patients with existing heart and kidney dysfunction, since over-hydration can result in pulmonary edema (fluid in the lungs), shortness of breath, the need for intubation, and even death. Thus, the patients at highest risk for RCN are those least likely to receive the only proven therapy for preventing RCN (I.V. hydration) due to the unpredictability of side effects from I.V. hydration.

A major limitation to the more widespread use of the already known therapeutic, or optimal, levels of I.V. hydration is the current inability to balance the amount of fluid going into the patient to the amount of fluid being removed or excreted from the patient. It is possible to have a nurse measure a patient's urine output frequently but this method is impractical as nurses are often responsible for the care of many patients. In addition, the only accurate method of measuring urine output is to place a catheter into the patient's urinary bladder. Without a catheter, the patient must excrete the urine that may have been stored in the bladder for several hours. During this time, the amount of I.V. hydration can be significantly less than the amount of urine produced by the kidneys and stored in the bladder, leading to dehydration. Since many patients do not normally have such a catheter during procedures using radiocontrast media, a valid measurement of urine output is not possible.

There seems to be indisputable scientific evidence that RCN in patients with even mild baseline renal insufficiency can lead to long term complications and even increased risk of mortality. This scientific knowledge has not yet been extended to daily clinical practice as routine monitoring of renal function post-catheterization is not usually performed and limits the identification of the known short-term clinical complications.

At the same time, there is a great deal of awareness in clinical practice that patients with serious renal insufficiency (serum creatinine (Cr)$\geq$2.0) often suffer serious and immediate damage from contrast. Many cardiologists go considerable length to protect these patients including slow, overnight hydration (an extra admission day), administration of marginally effective but expensive drugs, staging the procedure, or not performing procedures at all.

There are approximately 1 million inpatient and 2 million outpatient angiography and angioplasty procedures performed in the U.S. per year (based on 2001 data). Based on the largest and most representative published studies of RCN available to us (such as Mayo Clinic PCI registry of 7,586 patients) we believe that 4% of patients have serious renal insufficiency (Cr$\geq$2.0). This results in the initial market potential of 40 to 120 thousand cases per year from interventional cardiology alone. There is also a significant potential contribution from peripheral vascular procedures, CT scans and biventricular pacemaker leads placement. As the awareness of the RCN increases, the market can be expected to increase to 15% or more of all cases involving contrast.

According to the prior art, hydration therapy is given intravenously (I.V.) when someone is losing necessary fluids at a rate faster than they are retaining fluids. By giving the hydration therapy with an I.V., the patient receives the necessary fluids much faster than by drinking them. Also, dehydration can be heightened by hyperemesis (vomiting), therefore the I.V. method eliminates the need to take fluids orally. An anesthetized or sedated patient may not be able to drink. Hydration is used in clinical environments such as surgery, ICU, cathlab, oncology center and many others. At this time, hydration therapy is performed using inflatable pressure bags and/or I.V. pumps. A number of I.V. pumps on the market are designed for rapid infusion of fluids (as opposed to slow I.V. drug delivery) for perioperative hydration during surgery, ICU use and even emergency use for fluid resuscitation.

An infusion pump is a device used in a health care facility to pump fluids into a patient in a controlled manner. The device may use a piston pump, a roller pump, or a peristaltic pump and may be powered electrically or mechanically. The device may also operate using a constant force to propel the fluid through a narrow tube, which determines the flow rate. The device may include means to detect a fault condition, such as air in, or blockage of, the infusion line and to activate an alarm.

An example of a device for rapid infusion of fluids is the Infusion Dynamics (Plymouth Meeting, Pa.) Power Infuser. The Power Infuser uses two alternating syringes as a pumping engine. Since it is only intended to deliver fluids (not medication), the Power Infuser has accuracy of 15%. It provides a convenient way to deliver colloid as well as crystalloid for hydration during the perioperative period among other possible clinical settings. The Power Infuser provides anesthesiologists with the ability to infuse at rates similar to that seen with pressure bags, but with more exact volume control. The maximum infusion rate is 6 L/hr. It has the flexibility of infusing fluid at 0.2, 1, 2, 4 and 6 L/hr. A bolus setting of 250 mL will deliver that volume in 2.5 min. In a large blood loss surgical case, the use of Power Infuser enables large volumes of colloid to be delivered to restore hemodynamics.

It is also known in the art that loop diuretics such as Lasix furosemide (frusemide) reduce sodium reabsorption and consequentially reduce oxygen consumption of the kidney. They also reduce concentration of contrast agents in the urine-collecting cavities of the kidney. They induce diuresis (e.g., patient produces large quantities of very dilute urine) and help remove contrast out of the kidney faster. Theoretically, they should be the first line of defense against RCN. In fact, they were used to prevent RCN based on this assumption until clinical evidence suggested that they were actually deleterious. More recently, doubts have been raised regarding the validity of those negative clinical studies.

In two clinical studies by Solomon R., Werner C, Mann D. et al. "Effects of saline, mannitol, and furosemide to prevent acute decreases in renal function induced by radiocontrast agents", N Engl J Med, 1994; 331:1416-1420 and by Weinstein J. M., Heyman S., Brezis M. "Potential deleterious effect of furosemide in radiocontrast nephropathy", Nephron 1992; 62:413-415, as compared with hydration protocol, hydration supplemented with furosemide adversely affected kidney function in high-risk patients given contrast. Weinstein et al. found that furosemide-treated subjects lost 0.7 kg on average, whereas a 1.3-kg weight gain was noted in patients randomized to hydration alone, suggesting that in furosemide-treated subjects the hydration protocol has been insufficient and patients were dehydrated by excessive diuresis.

The clinical problem is simple to understand: diuresis is widely variable and unpredictable but the fluid replacement (hydration) at a constant infusion rate is prescribed in advance. To avoid the risk of pulmonary edema, fluid is typically given conservatively at 1 ml/hr per kg of body weight. The actual effect of diuretic is typically not known for 4 hours (until the sufficient amount of urine is collected and measured) and it is too late and too difficult to correct any imbalance. Meanwhile, patients could be losing fluid at 500 ml/hour while receiving the replacement at only 70 ml/hour. The effects of forced diuresis without balancing are illustrated in the research paper by Wakelkamp et. al. "The Influence of Drug input rate on the development of tolerance to furosemide" Br J. Clin. Pharmacol. 1998; 46: 479-487. In that study, diuresis and natriuresis curves were generated by infusing 10 mg of I.V. furosemide over 10 min to human volunteers. From that paper it can be seen that a patient can lose 1,300 ml of urine within 8 hours following the administration of this potent diuretic. Standard unbalanced I.V. hydration at 75 ml/h will only replace 600 ml in 8 hours. As a result the patient can lose "net" 700 ml of body fluid and become dehydrated. If such patient is vulnerable to renal insult, they can suffer kidney damage.

To illustrate the concept further, the effects of diuretic therapy on RCN were recently again investigated in the PRINCE study by Stevens et al. in "A Prospective Randomized Trial of Prevention Measures in Patients at High Risk for Contrast Nephropathy, Results of the PRINCE. Study" JACC Vol. 33, No. 2, 1999 February 1999:403-11. This study demonstrated that the induction of a forced diuresis while attempting to hold the intravascular volume in a constant state with replacement of urinary losses provided a modest protective benefit against contrast-induced renal injury, and importantly, independent of baseline renal function. This is particularly true if mean urine flow rates were above 150 ml/h. Forced diuresis was induced with intravenous crystalloid, furosemide, and mannitol beginning at the start of angiography.

The PRINCE study showed that, in contrast to the Weinstein study, forced diuresis could be beneficial to RCN patients if the intravascular volume was held in a constant state (no dehydration). Unfortunately, there are currently no practical ways of achieving this in a clinical setting since in response to the diuretic infusion the patient's urine output changes rapidly and unpredictably. In the absence of special equipment, it requires a nurse to calculate urine output every 15-30 minutes and re-adjust the I.V. infusion rate accordingly. While this can be achieved in experimental setting, this method is not possible in current clinical practice where nursing time is very limited and one nurse is often responsible for monitoring the care of up to ten patients. In addition, frequent adjustments and measurements of this kind often result in a human error.

Forced hydration and forced diuresis are known art that has been practiced for a long time using a variety of drugs and equipment. There is a clear clinical need for new methods and devices that will make this therapy accurate, simple to use and safe.

In addition, patients involved with a variety of medical procedures such as cardiac surgery often retain water. Some patients, such as heart failure patients, may be overloaded with fluid. Often, a diuretic such as Lasix is administered and a nurse is directed to check when the patient has expelled a certain amount of urine. Often, the patient is weighed to determine the amount of fluid loss.

Nurses, however, are often very busy and it is possible that a patient, once given a diuretic, could expel urine to the point the patient becomes hydrated. Also, to prevent hydration, the nurse may administer a hydration fluid such as saline. There is no known prior art system which achieves automatic balanced hydration in a patient. The applicant's co-pending applications directed to a balanced hydration system are incorporated herein by this reference. They are U.S. patent application Ser. No. 10/936,945 filed Sep. 9, 2004 entitled "Patient Hydration System and Method"; U.S. patent application Ser. No. 11/408,851 filed Apr. 21, 2006 entitled "Patient Hydration System With a Redundant Monitoring of Hydration Fluid Infusion"; U.S. patent application Ser. No. 11/408,391 filed Apr. 21, 2006 entitled "Patient Hydration System With Abnormal Condition Sensing"; U.S. patent application Ser. No. 11/409,171 filed Apr. 21, 2006 entitled "Patient Hydration System With Hydration State Detection"; and U.S. patent application Ser. No. 11/580,354 filed Oct. 13, 2006 entitled "Patient Connection System For a Balance Hydration Unit".

SUMMARY OF THE INVENTION

It is therefore an object of this invention to provide a patient hydration system and method.

It is a further object of this invention to provide such a system and method which prevents kidney damage in a patient.

It is a further object of this invention to provide such a system and method which protects the patient undergoing a medical procedure, for example, a procedure involving a radiocontrast agent.

It is a further object of this invention to provide such a system and method which incorporates a balancing feature intended to prevent dehydration, overhydration, and to maintain a proper intravascular volume.

It is a further object of this invention to provide a balanced diuresis method which automatically balances fluid loss in the urine.

It is a further object of this invention to provide such a system and method which is accurate, easy to implement, and simple to operate.

It is a further object of this invention to provide such a system and method which is particularly useful in the clinical setting of forced diuresis with drugs known as I.V. loop diuretics.

The subject invention results from the realization that patient dehydration and over hydration in general can be prevented by automatically measuring the urine output of the patient and adjusting the rate of delivery of a hydration fluid to the patient to achieve, as necessary, a zero, positive, or negative net fluid balance in the patient.

This subject invention features, in one embodiment, a patient hydration system. An infusion subsystem is responsive to a source of hydration fluid for infusing the patient with hydration fluid. A urine output measurement subsystem determines the amount of urine output by the patient. A controller is responsive to the urine output measurement subsystem and is configured to receive a setting corresponding to an amount of urine to be output by the patient. When or after the urine output measurement subsystem indicates the set amount of urine has been output by the patient, the infusion subsystem is controlled to administer hydration fluid to the patient based on the patient's further urine output.

In one example, the urine output measurement subsystem includes a urine reservoir connected to the patient and a weighing mechanism for weighing the urine reservoir. Typically, the infusion subsystem includes an infusion pump. There may be a console for mounting on an IV pole. A first attachment mechanism extends from the console for hanging a urine collection chamber. A first weighing device is associated with the console and responsive to the first attachment. A second attachment extends from the console for hanging a source of hydration fluid. A second weighing device is associated with the console and is responsive to the second attachment for weighing the source of hydration fluid. An infusion pump is typically integrated with the console and configured to pump hydration fluid from the source of hydration fluid to the patient. The controller is responsive to the first and second weighing devices and is configured to control the infusion pump to hydrate the patient based on the patient's urine output.

In one embodiment, a patient hydration method for a patient to whom a diuretic has been administered includes setting a patient hydration subsystem to infuse the patient with hydration fluid after a predetermined amount of urine is output by the patient and which thereafter adjusts the infusion rate of the infusion subsystem based on the urine output of the patient. Typically, the patient's urine output and the source of hydration fluid are weighed. Controlling the hydration fluid infusion rate typically includes controlling an infusion pump.

One patient hydration method in accordance with this invention features setting a desired patient urine output, automatically determining the amount of urine output by the patient, and when or after the set desired patient urine output has been output by the patient, automatically administering hydration fluid to the patient based on the patient's urine output thereafter.

In another example, the subject invention features a patient monitoring system. A urine output measurement subsystem automatically determines the amount of urine output by the patient. A controller is responsive to the urine output measurement subsystem and is configured to receive a setting corresponding to an amount of urine desired to be output by the patient. When or after the urine output measurement subsystem indicates the set amount of urine has been output by the patient, an action is taken. The action may be activating an alarm and/or controlling an infusion subsystem to administer hydration fluid to the patient based on the patient's urine output.

One patient monitoring method comprises setting a desired amount of urine to be output by the patient, automatically determining the amount of urine output by the patient, and when the set amount of urine has been output by the patient, automatically taking an action.

An example of one patient hydration system includes an infusion subsystem responsive to a source of hydration fluid for infusing the patient with hydration fluid, a urine output measurement subsystem for determining the amount of urine output by the patient, and a controller, responsive to the urine output measurement subsystem and configured to receive a setting corresponding to a desired amount of urine to be output by the patient. When or after the urine output measurement subsystem indicates the set amount of urine has been output by the patient, an action is taken.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
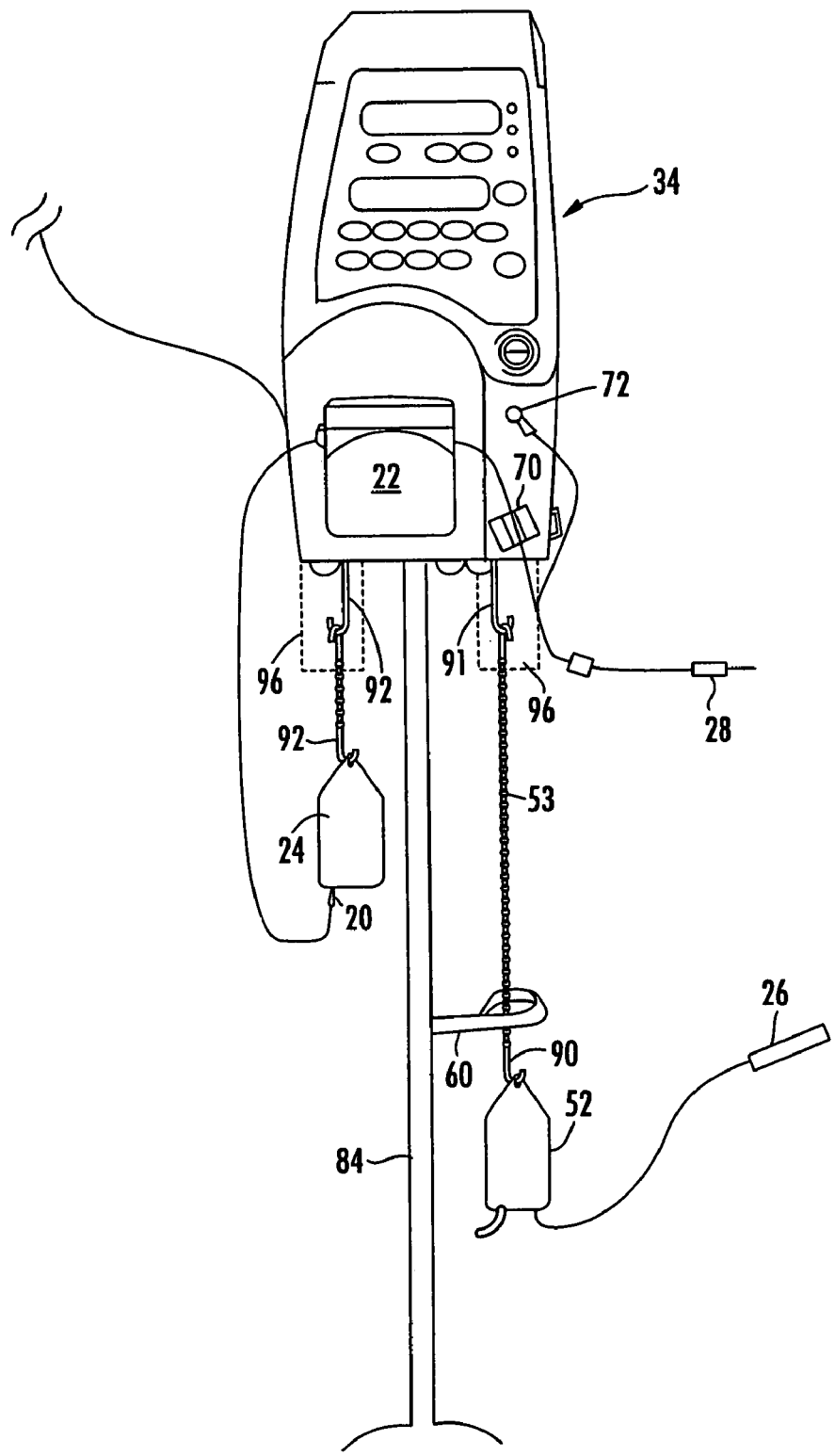
FIG. 1 is a schematic front view of an example of a patient hydration system in accordance with the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

One preferred example of a patient hydration system according to this invention includes unit 34, FIG. 1 typically mounted on IV pole 84. Unit 34 has programmable controller electronics therein. There is an infusion subsystem including pump 22 responsive to source of infusion fluid 24 for infusing a patient with hydration fluid. There is also a urine output measurement subsystem for determining the amount of urine output by the patient. In this particular example, source of infusion fluid bag 24 is hung on hook 92 and urine collection chamber or bag 52 is hung on hook 91 via chain 53 and hook 90. Unit 34 includes one or more weight scales such as an electronic strain gage or other means to periodically detect the weight of the collected urine in bag 52 and, if desired, the weight of the remaining hydration fluid in bag 24. Hooks 91 and 92 are connected to a system of levers which translates force to a scale such as a strain gage within unit 34. The strain gage converts force into an electronic signal that can be read by a controller. Suitable electronic devices for accurately measuring the weight of a suspended bag with urine are available from Strain Measurement Devices, 130 Research Parkway, Meriden, Conn., 06450. These devices include electronic and mechanical components necessary to accurately measure and monitor weight of containers with medical fluids such as one or two-liter plastic bags of collected urine. For example, the overload proof single point load cell model S300 and the model S215 load cell from Strain Measurement Devices are particularly suited for scales, weighing bottles or bags in medical instrumentation applications. Options and various specifications and mounting configurations of these devices are available. These low profile single point sensors are intended for limited space applications requiring accurate measurement of full-scale forces of 2, 4, and 12 pounds-force. They can be used with a rigidly mounted platform or to measure tensile or compressive forces. A 10,000Ω wheatstone bridge offers low power consumption for extended battery life in portable products. Other examples of gravimetric scales used to balance medical fluids using a controller controlling the rates of fluid flow from the pumps in response to the weight information can be found in U.S. Pat. Nos. 5,910,252; 4,132,644; 4,204,957; 4,923,598; and 4,728,433 incorporated herein by this reference.

It is understood that there are many ways known in the art of engineering to measure weight and convert it into computer inputs. Regardless of the implementation, the purpose of the weight measurement is to detect the increasing weight of the collected urine in the bag 52 and to adjust the rate of infusion or hydration based on the rate of urine flow by the patient by controlling infusion pump 22.

Unit 34 is also typically equipped with the user interface. The interface allows the user to set (dial in) the two or more parameters of therapy such as the duration of hydration and the desired net fluid balance at the end. The amount of urine which must be output by the patient before balancing begins can also be set. The net fluid balance can be zero if no fluid gain or loss is desired. Display indicators on the console show the current status of therapy: the elapsed time, the net fluid gain or loss, the amount of fluid infused, the amount of fluid loss, the loss rate, and/or the infusion rate.

The user interface may also include alarms. The alarms notify the user of therapy events such as an empty fluid bag or a full collection bag as detected by the weight scale. In one proposed embodiment, the urine is collected by gravity. If urine collection unexpectedly stops for any reason, the system will reduce and, if necessary, stop the IV infusion of fluid and alarm the user. Alternatively, the console can include the second (urine) pump similar to infusion pump 22. This configuration has an advantage of not depending on the bag height for drainage and the capability to automatically flush the catheter if it is occluded by temporarily reversing the pump flow direction.

Infusion pump 22 pumps infusion fluid from bag 24 into the patient and is controlled by the controller electronics within the unit which monitors the weight of the urine in urine collection bag 52. In this way, the patient is properly hydrated and the infusion rate of infusion pump 22 is automatically adjusted to achieve, as necessary, a zero, positive, or negative net fluid balance in the patient.

The electronic controller may also incorporate a more advanced feature allowing the physician to set a desired (for example positive) hydration net goal. For example, the physician may set the controller to achieve positive or negative net gain of 400 ml in 4 hours. The controller calculates the trajectory and adjusts the infusion pump flow rate setting to exceed the urine output accordingly. For example, to achieve a positive net gain of 400 ml over 4 hour, the controller may infuse 25 ml of hydration fluid every 15 minutes in addition to the volume of urine made by the patient in each 15 minute interval. See also co-pending U.S. application Ser. Nos. 11/408,391; 11/408,851; and 11/409,171 filed Apr. 21, 2006 which are incorporated herein by this reference.

In accordance with one example, the infusion set includes infusion bag "spike" connector 20 received in infusion fluid bag 24, luer connector 28 for receiving an IV needle, and tubing extending therebetween and placed within infusion pump 22. The urine collection set typically includes urine collection bag 52, Foley catheter connector 26 for connection to a Foley catheter, and tubing extending between the urine collection bag and connector 26. The infusion set and the urine collection set are preferably placed together as a kit for the hydration unit in sealed bag for storage in a sterile fashion until ready for use. The integrated infusion set includes an IV bag spike, a Luer-to-Foley connector for priming, and a urine collection set includes an integrated urine bag.

The power requirements are typically 115/220 VAC, 60/50 Hz, 25 VA. An auxiliary ground post (potential equalization) for the device is on the rear of the case (not shown). An RS 232 port is also provided. When mounted on an I.V. Pole, the system requires an area of approximately 20×20 inches. Console 34 is placed on the pole so that the urine collection bag 504 is above floor level and not touching the floor or other equipment. Urine collection bag chain 53 is passed through motion restrictor ring 60 to prevent excessive swinging of the bag. Urine collection bag 52 is below the level of patient to facilitate urine drainage, and urine 52 and hydration fluid 24 bags are hanging freely on hooks 90 and 92, respectively, and not supported or impeded. Protection tubes 94 and 96 shown in phantom may be provided about hooks 91 and 92.

The system maintains hydration balance by measuring patient urine output and infusing hydration fluid (prescribed by physician) into the patient I.V. to balance the fluid lost in urine. In addition to urine volume replacement, the system implements a user-set net fluid gain or loss. Net fluid gain is defined as the amount of fluid in ml/hour infused into I.V. in addition to the replaced volume of urine. The system also allows rapid infusion of a Bolus of fluid at the user request. The amount of Bolus can be selected by user and typically the bolus is infused over 30 minutes. Bolus is infused in addition to the Net Fluid Gain and the replaced volume of urine. Unit 34 typically includes a microcontroller device that has means for measuring urine output and the ability to infuse hydration fluid into the patient. The infusion set allows the console to pump fluid from a hydration fluid bag to the patient at a controlled rate. The disposable urine collection set collects the patient's urine to allow it to be measured accurately. Unit 34 is also equipped with an internal battery that can sustain operation in the event of power outage or during short periods of time, for example, when the patient is moved. Unit 34 may include roller pump 22, a user interface, two weighing scales (not shown), air detector 70, post-pump pressure sensor 72, an electrical connector for AC power, and mechanical interfaces for holding the set in place. Console 34 controls the rate at which fluid is infused and monitors urine volume by weight measurement.

Figure 2:
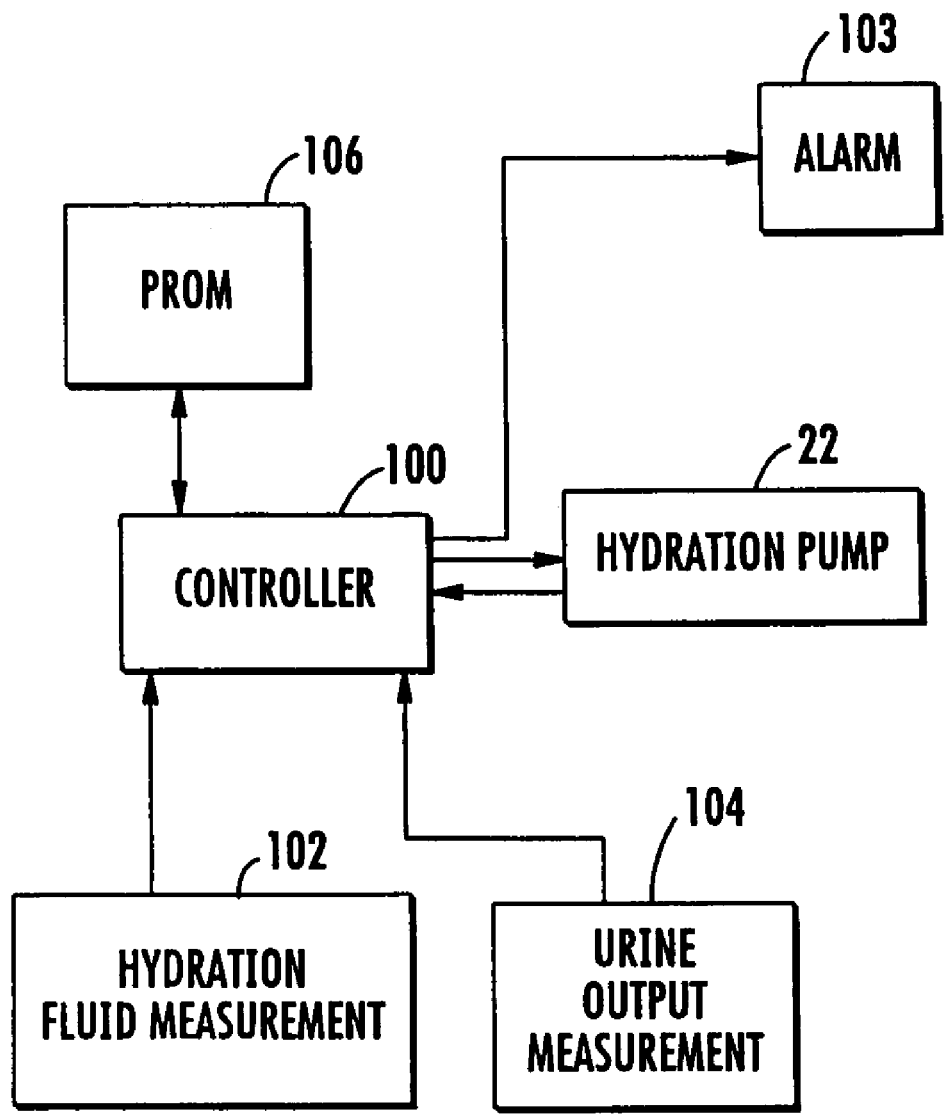
FIG. 2 is a block diagram showing several primary components of one embodiment of a patient hydration system in accordance with the subject invention wherein the weight of the urine output by a patient is measured and used as an input to control the infusion rate of an infusion pump.

In the subject invention, controller 100, FIG. 2 (a microprocessor or microcontroller or other circuitry (e.g., a comparator) in console 34, FIG. 1) controls hydration pump 22 to infuse the patient with hydration fluid based on the patient's urine output and keeps track of the hydration fluid injected in two ways to provide safety and redundancy. The preferred hydration fluid measurement subsystem includes, first, as discussed above, the weight of hydration fluid source 24, FIG. 1 which is monitored as shown at 102 in FIG. 2. Urine output is also monitored as shown at 104. In addition, the operation history of infusion pump 22 may be monitored by controller 100. Controller 100 may store values representing both of these measurements in a memory such as PROM 106 and controller 100 is programmed as shown in FIG. 3 to store the hydration fluid amounts administered via the hydration fluid measurement strain gauge, and controller 100 is also programmed to store the hydration fluid amount administered by monitoring of the hydration pump operation history.

Figure 3:
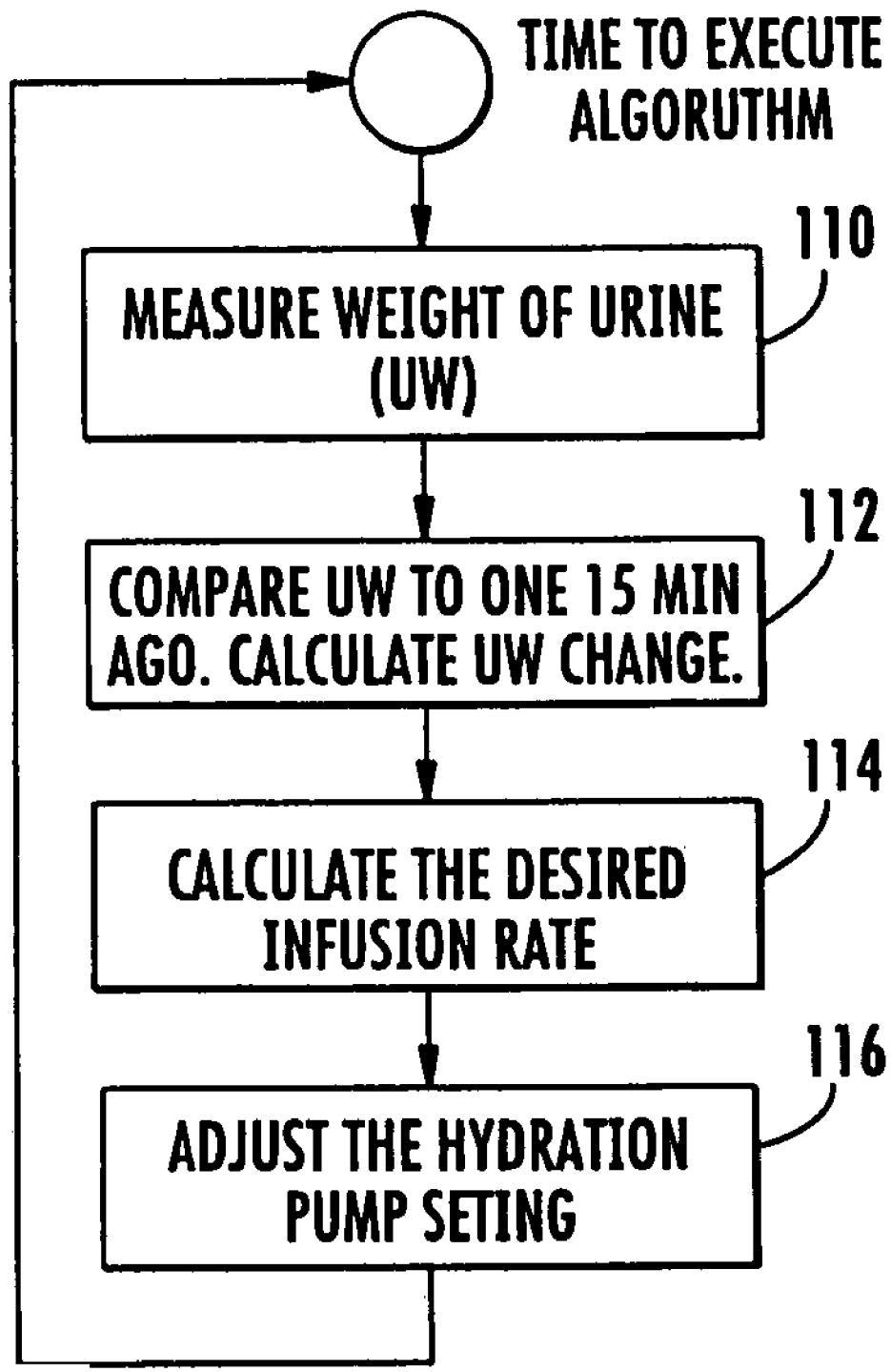
FIG. 3 is a flow chart depicting one example of the software associated with the controller of this invention and the method of adjusting the infusion rate based on the amount of urine output by the patient.

FIG. 3 illustrates an algorithm that can be used by the controller software of controller 100, FIG. 2 to execute the desired therapy. The algorithm is executed periodically based on a controller internal timer clock. It is appreciated that the algorithm can be made more complex to improve the performance and safety of the device. Controller 100, FIG. 2 is programmed to determine the rate of change of the urine weight, steps 110 and 112, FIG. 3 to calculate a desired infusion rate based on the rate of change of the urine weight, step 114, and to adjust the infusion rate of the infusion pump 22, FIG. 1 based on the calculated desired infusion rate, step 116, FIG. 3.

As discussed in the Background section above, patients involved with a variety of medical procedures such as cardiac surgery often retain water or, a patient may be overloaded with fluid. Often, a diuretic such as Lasix is administered and a nurse is directed to check when the patient has expelled a certain amount of urine.

Nurses, however, are often very busy and it is possible that a patient, once given a diuretic, could expel urine to the point the patient becomes dehydrated. To prevent or correct for dehydration, the nurse may administer a hydration fluid such as saline.

Figure 4:
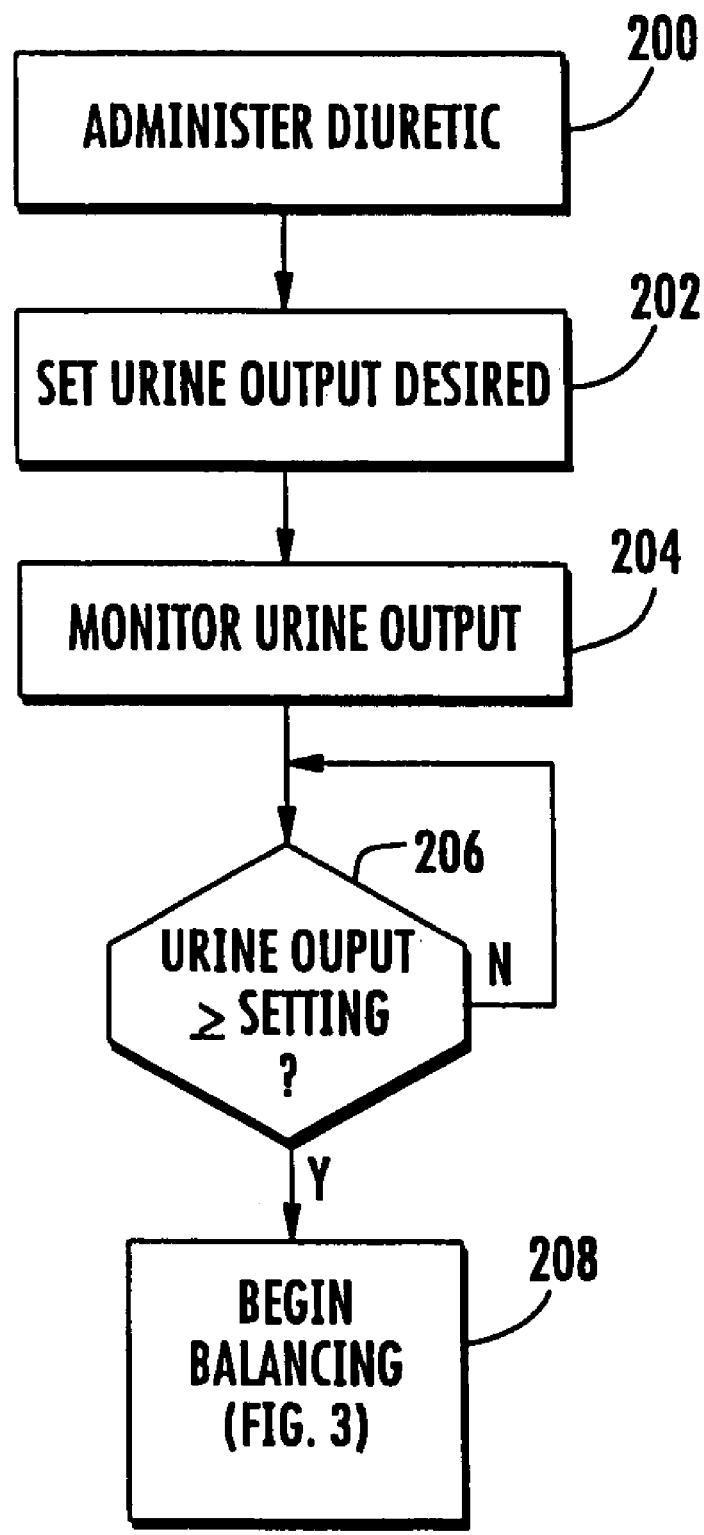
FIG. 4 is a flow chart showing an embodiment of the subject invention wherein fluid balancing begins after a set urine output is reached.

In accordance with the subject invention, a diuretic is administered, step 200, FIG. 4 typically because a patient has retained fluids and it is desired that the patient take off a certain amount of fluid, e.g., 400 ml. The desired urine output is set, step 202 by an input to the user interface of unit 34, FIG. 1. Controller 100, FIG. 2 is programmed, step 204, FIG. 4 to monitor the urine output by the patient typically by the weight of urine in urine bag 52, FIG. 1. The rate of urine output can also be calculated and displayed. Other urine output measurement subsystems, however, are within the scope of the subject invention. In step 206, FIG. 4, controller 100, FIG. 2 is programmed to determine when the patient's urine output is equal to or greater than the amount set in step 202, FIG. 4. Once the set amount has been expelled by the patient, balancing may begin as discussed above with respect to FIG. 3, step 208, FIG. 4.

In this way, a physician can prescribe, for a patient who has retained fluids, a goal of a net fluid loss of, for example, 400 ml. Once this amount of urine has been expelled by the patient (with or without the use of a diuretic), unit 34 begins fluid balancing by replacing urine loss thereafter by infusion of a hydration fluid such as saline. The nurse or attendant can set a net zero loss, a positive fluid gain, or a negative fluid loss at any time. In another example, a physician prescribes a net fluid loss of 1 liter every hour. The patient, as measured by the urine output measurement subsystem, outputs 1 liter in ½ hour. Controller 100, FIG. 2 then controls infusion pump 22, FIG. 1 to infuse saline at a rate equal to the patient's urine output in the next half hour. Balancing then stops and then, in the second hour, the patient expels 1 liter in 45 minutes. Controller 100, FIG. 2 begins balancing again for the last 15 minutes of the hour, and so on.

In a less complex embodiment, there is no fluid infusion into the patient. Instead, an alarm or other indication is provided by unit 34, FIG. 1 once the prescribed fluid loss has been reached and only steps 200-206, FIG. 4 are carried out by controller 100, FIG. 2. Once the set amount of urine has been output by the patient, controller 100, FIG. 2 may take any number of actions including, but not limited to, balancing and/or activating an alarm as shown at 103 in FIG. 2. Also, the user interface of unit 34 can display the fluid loss rate and the nurse can begin infusion at that rate in the case where unit 34 lacks an automatic infusion subsystem.

Although specific features of the invention are shown in some drawings and not in others, this is for convenience only as each feature may be combined with any or all of the other features in accordance with the invention. For example, there are other ways to determine a patient's urine output and other ways to quantify the amount of hydration fluid administered to the patient. There are also other ways to redundantly check the amount of hydration fluid administered the patient. Also, the words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A method of addressing contrast induced nephropathy, the method comprising:
   injecting a contrast agent into a patient;
   imaging the patient; and
   injecting a diuretic into the patient to induce diuresis; and
   further inducing diuresis to drive any contrast agent through the patient's kidneys to reduce its toxic effects on the kidneys and prevent damage to the kidneys by:
      setting a desired fluid balance,
      collecting urine expelled by the patient in a urine collection bag,
      weighing the urine collection bag,
      determining, based on the weight of the urine collection bag, when the patient has expelled a predetermined amount of urine,
      after the predetermined amount of urine has been expelled by the patient, employing a pump to infuse the patient with fluid from a fluid source,
      weighing the fluid source to provide an indication regarding the amount of fluid infused into the patient, and
   automatically adjusting the pump based on the set desired fluid balance, the weight of the urine collection bag, and the weight of the fluid source and controlling the amount of fluid infused into the patient based on the amount of urine expelled by the patient,
   determining if a bolus amount of infusion fluid is required for the patient in addition to the fluid infused to achieve the desired fluid balance, and
   if a bolus amount was set, automatically controlling the pump to infuse the set bolus amount into the patient.

* * * * *